US006639113B2

(12) United States Patent
Runge et al.

(10) Patent No.: US 6,639,113 B2
(45) Date of Patent: Oct. 28, 2003

(54) PRODUCTION OF DRY POWDERS OF ONE OR MORE OXYGENATED CAROTENOIDS

(75) Inventors: Frank Runge, Friedelsheim (DE); Erik Lüddecke, Mutterstadt (DE); Helmut Auweter, Limburgerhof (DE); Angelika-Maria Pfeiffer, Birkenheide (DE); Willy Hinz, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 7 days.

(21) Appl. No.: 10/015,560

(22) Filed: Dec. 17, 2001

(65) Prior Publication Data

US 2002/0165285 A1 Nov. 7, 2002

(30) Foreign Application Priority Data

Dec. 21, 2000 (DE) .......................... 100 64 387

(51) Int. Cl.[7] .................. C07C 45/00; C12P 23/00; A61K 9/14; A61K 9/16
(52) U.S. Cl. ................. 568/347; 568/367; 568/377; 568/816; 568/834; 435/67; 424/489; 424/491; 424/498
(58) Field of Search ................ 568/347, 367, 568/377, 816, 834; 435/67; 424/489, 491, 498

(56) References Cited

U.S. PATENT DOCUMENTS

| 3,110,598 A | 11/1963 | Mueller et al. ........... 99/148 |
| 4,522,743 A | 6/1985 | Horn et al. ............... 252/311 |
| 5,356,636 A | 10/1994 | Schneider et al. ........ 424/489 |
| 5,364,563 A | 11/1994 | Cathrein et al. .......... 252/311 |
| 5,976,575 A | 11/1999 | Gellenbeck ............... 424/489 |
| 6,235,315 B1 | 5/2001 | Runge et al. ............. 424/489 |

FOREIGN PATENT DOCUMENTS

| CA | 2194796 | 1/1996 |
| DE | 1 211 911 | 3/1966 |
| DE | 44 24 085 | 1/1996 |
| DE | 196 52 287 | 7/1997 |
| DE | 198 41 930 | 3/2000 |
| EP | 0 065 193 | 11/1982 |
| EP | 0 410 236 | 1/1991 |
| EP | 0 498 824 | 8/1992 |
| EP | 0 547 422 | 6/1993 |
| EP | 0 807 431 | 11/1997 |
| EP | 0 937 412 | 8/1999 |
| GB | 887883 | 1/1962 |
| WO | WO 91/06292 | 5/1991 |
| WO | WO 94/19411 | 9/1994 |
| WO | WO 96/08977 | 3/1996 |

OTHER PUBLICATIONS

Manz, "Die Anwendung und Bedeutung von Synthetischen Carotinoiden in der Lebens–und Futtermittelsowie in der pharmazeutischen Industrie " Chimie No. 21 (1967) pp. 329–335.
Salares et al. "Excited State (Exciton) Interaction in Polyene Aggregates" Jrnl of Raman Spectroscopy vol. 6, No. 6, (1977) pp. 282–288.
Ruban et al. "Aggregation of Higher Plant Xanthophylls: Differences in Absorption Spectra and in the Dependency on Solvent Polarity" Jnl. Photochem, Photobiol. vol. 21 (1993) pp. 229–234.
Song et al. "On the Photoreceptor Pigment For Photoropism and Phototaxis: Is a Carotenoid the Most Likely Candidate?" Photochemistry and Photobiology vol. 19 (1974) pp. 435–441.

Primary Examiner—Samuel Barts
Assistant Examiner—Sikarl A. Witherspoon
(74) Attorney, Agent, or Firm—Keil & Weinkauf

(57) ABSTRACT

A process is described for preparing dry powders of one or more oxygenated carotenoids by
  a) dispersing one or more oxygenated carotenoids in an aqueous molecular dispersion or colloidal dispersion of a protecting colloid and
  b) converting the dispersion formed into a dry powder by removing the water and any solvents additionally used and drying, in the presence or absence of a coating material, which comprises using as protecting colloid in process step a) at least one partially hydrolyzed soybean protein having a degree of hydrolysis greater than 5%.

13 Claims, No Drawings

PRODUCTION OF DRY POWDERS OF ONE OR MORE OXYGENATED CAROTENOIDS

The invention relates to a process for producing dry powders of one or more oxygenated carotenoids, in particular dry powders, comprising carotenoids selected from the group consisting of astaxanthin, canthaxanthin, lutein, zeaxanthin, citranaxanthin and β-apo-8'-carotinic acid ethyl ester.

The carotenoid class of substances is classified into two main groups, carotenes and xanthophylls. In contrast to the carotenes, which are purely polyene hydrocarbons, for example β-carotene or lycopene, in the xanthophylls, oxygen functions, such as hydroxyl, epoxy and/or oxo groups also occur. Typical representatives of this group are, inter alia, astaxanthin, canthaxanthin, lutein and zeaxanthin.

Oxygenated carotenoids are widespread in nature and occur, inter alia, in corn (zeaxanthin), in green beans (lutein), in capsicum (capsanthin), in egg yolks (lutein) and in crabs and salmon (astaxanthin), in which case they give the characteristic coloration to these foods.

These polyethers which are not only accessible by synthesis, but can also be isolated from natural sources, are important pigments for the food and feed industries and for the pharmaceutical sector and, in the case of astaxanthin, are active compounds having provitamin A activity in salmon.

Xanthophylls, like all carotenoids, are insoluble in water, whereas in fats and oils, however, only low solubility is found. This restricted solubility and the high sensitivity to oxidation oppose direct use of the relatively coarse-grained products obtained in synthesis in the pigmentation of foods and feeds, since the substances in coarsely crystalline form give only poor pigmentation results. These effects which are disadvantageous for the practical use of xanthophylls are pronounced in particular in aqueous medium.

Only by means of specifically produced formulations in which the active compounds are present in finely divided form and, if appropriate, are protected against oxidation by protective colloids, can improved color yields be achieved in the direct pigmentation of foods. In addition, these formulations used in feeds lead to a higher bioavailability of the xanthophylls and thus indirectly to improved pigmentation effects, for example in the pigmentation of egg yolks or fish.

To improve the color yields and to increase the absorbability and bioavailability, various methods have been described which all have the purpose of decreasing the crystallite size of the active compounds and bringing it to a particle size range of smaller than 10 μm.

Numerous methods, inter alia described in Chimia 21, 329 (1967), WO 91/06292 and in WO 94/19411, make use of grinding carotenoids by means of a colloid mill and thus achieve particle sizes of from 2 to 10 μm.

In addition there are a number of combined emulsification/spray-drying processes, as described, for example, in DE-A-12 11 911 and EP-A-0 410 236.

According to European patent EP-B-0 065 193, finely divided pulverulent carotenoid preparations are prepared by dissolving a carotenoid in a volatile water-miscible organic solvent at elevated temperatures, if appropriate under elevated pressure, precipitating out the carotenoid by mixing with an aqueous solution of a protecting colloid and then spray-drying it.

A similar process for producing finely divided pulverulent carotenoid preparations is described in EP-A-0 937 412, using water-immiscible solvents.

However, in the case of the nanoparticulate active compound dispersions of xanthophylls produced in accordance with EP-B-0 065 193, the following phenomena may frequently be observed.

The aqueous xanthophyll-containing active compound dispersions are frequently, in particular during concentration, colloidally unstable. As a result of flocculation of the active compound particles which in part sediment, in part cream in the course of this, further conversion of the dispersion into a dry powder is no longer possible.

In the case of xanthophylls containing carbonyl functions, in addition, the gelatin used as protecting colloid can crosslink, so that a gel is formed that can no longer be redispersible and which also cannot be converted into a dry powder.

Thus the high requirements made of xanthophyll-containing formulations with respect to pigmenting action and bioavailability cannot always be met, owing to the problems with the abovementioned process described.

A disadvantage of gelatins is also their highly adhesive property. Using the drying methods customary for liquid systems, such as spray-drying, or spray-fluidized-bed drying, filament formation or encrustations can occur when gelatin-containing products are used.

In addition, gelatin-containing products have constantly decreasing consumer acceptance.

Frequently, only relatively low concentrations of fat-soluble substances can be incorporated into other frequently used protecting colloids, such as gum arabic, starch, dextrins, pectin or tragaxanth. Furthermore, gum arabic, in the past, as a result of harvest failures, has not always been available, nor in sufficient quality.

Synthetic colloids such as polyvinylpyrrolidone or partially synthetic polymers such as cellulose derivatives also exhibit restricted emulsifying capacity and are not always accepted, especially in the foods sector.

DE-A-44 24 085 describes the use of partially hydrolyzed soybean proteins as protecting colloids for fat-soluble active compounds. The soybean proteins disclosed here have a degree of hydrolysis of from 0.1 to 5%.

A disadvantage of the abovementioned soybean proteins is frequently their poor water solubility, inadequate emulsifying properties and their tendency to crosslink, which is undesirable, particularly for the production of dry powders which can be redispersed in water.

It is an object of the present invention, therefore, to propose processes for producing dry powders of oxygenated carotenoids using protecting colloids which do not have the abovementioned disadvantages of the prior art.

We have found that this object can be achieved, surprisingly, by a process for producing dry powders of one or more oxygenated carotenoids by a) dispersing one or more oxygenated carotenoids in an aqueous molecular dispersion or colloidal dispersion of a protecting colloid and b) converting the dispersion formed into a dry powder by removing the water and any solvents additionally used and drying, in the presence or absence of a coating material, which comprises using as protecting colloid in process step a) at least one partially hydrolyzed soybean protein having a degree of hydrolysis greater than 5%.

According to the invention, the protecting colloid is a partially hydrolyzed soybean protein that has a degree of hydrolysis (DH) greater than 5%, preferably from 6 to 20%, particularly preferably from 6 to 12%, very particularly preferably from 6 to 9%. The degree of hydrolysis "DH" is defined as follows:

$$DH = \frac{\text{Number of peptide bonds cleaved}}{\text{Total number of peptide bonds}} \times 100\%$$

The degree of hydrolysis can be determined by the "pH-Stat-Method", as described by C. F. Jacobsen et al. in "Methods of Biochemical Analysis", Vol. IV, pp. 171–210, Interscience Publishers Inc., New York 1957.

The partial hydrolysis is generally performed enzymatically, with as suitable enzymes, proteases from plants, microorganisms and fungi, or animal proteases, coming into consideration. Preferably, the partial hydrolysis is performed using the plant protease bromelain.

The soybean proteins used are customarily commercial soybean protein isolates and soybean protein concentrates with protein contents of 70 to 90% by weight, the remaining 10 to 30% by weight being more or less undefined other plant constituents, soybean proteins which are preferably used in this context are non-genetically-modified soybean proteins.

The soybean protein-isolates are incubated with the enzyme in an aqueous medium, preferably at from 50 to 70° C. and at pHs from 7 to 9. The suitable ratio of protein to enzyme can be determined in individual cases for the desired degree of hydrolysis in laboratory experiments which are simple for those skilled in the art.

The aqueous soybean protein hydrolysate solutions are generally prepared in such a manner that the protein content is from 6 to 10% by weight.

The weight-average molecular weight of the inventively used partially hydrolyzed soybean proteins is generally in the range from 15000 to 250000, preferably from 25000 to 220000, particularly preferably from 50000 to 200000, very particularly preferably in the range from 120000 to 180000.

It is also possible to use as protecting colloids in the inventive process mixtures of partially hydrolyzed soybean proteins of different degrees of hydrolysis, or mixtures of partially hydrolyzed and non-hydrolyzed soybean proteins. With these mixtures, their weight-average molecular weights are also in the abovementioned ranges.

The term dispersing is preferably producing aqueous suspensions and aqueous emulsions. Particularly preferably, the dispersion step a) is the production of a suspension of one or more oxygenated carotenoids in an aqueous molecular dispersion or colloidal dispersion of a partially hydrolyzed soybean protein in which the disperse phase comprises at least one of the active compounds as nanoparticulate particles.

In a preferred embodiment of the above process, the suspension produced in process step a) is ground before conversion into a dry powder. In this case, the active compound is preferably suspended in crystalline form before the grinding operation.

The grinding can be performed here in a manner known per se, for example using a ball mill. Depending on the type of mill used, grinding is performed until the particles have a mean particle size determined via Fraunhofer diffraction D[4,3] of from 0.1 to 100 $\mu$m, preferably from 0.2 to 50 $\mu$m, particularly preferably from 0.2 to 20 $\mu$m, very particularly preferably from 0.2 to 5 $\mu$m, in particular from 0.2 to 0.8 $\mu$m. The term D[4,3] denotes the volume-weighted mean diameter (see the Handbook to Malvern Mastersizer S, Malvern Instruments Ltd., UK).

Further details on grinding and the apparatuses used for this may be found, inter alia, in Ullmann's Encyclopedia of Industrial Chemistry, Sixth Edition, 1999, Electronic Release, Size Reduction, Chapter 3.6.: Wet Grinding, and in EP-A-0 498 824.

In a variant of the inventive process which is also preferred, the dispersion in stage a) comprises the following steps:

$a_1$) dissolving one or more oxygenated carotenoids in a water-miscible organic solvent or in a mixture of water and a water-miscible organic solvent or $a_2$) dissolving one or more oxygenated carotenoids in a water-immiscible organic solvent and $a_3$) mixing the solution obtained after $a_1$) or $a_2$) with an aqueous molecular dispersion or colloidal dispersion of a partially hydrolyzed soybean protein having a degree of hydrolysis greater than 5%, the hydrophobic phase of the carotenoid being produced as nanodisperse phase.

Depending on the type of solvents used, the nanodisperse phase in step $a_3$) can be solid nanoparticles (suspension) or nano droplets (emulsion).

The water-miscible solvents used in stage $a_1$) are primarily water-miscible, thermally stable, volatile solvents containing only carbon, hydrogen and oxygen, such as alcohols, ethers, esters, ketones and acetals. Expediently, those solvents are used that are at least 10% water-miscible, have a boiling point below 200° C. and/or have fewer than 10 carbons. Particular preference is given to methanol, ethanol, n-propanol, isopropanol, 1,2-butane-1-diol methyl ether, 1,2-propane-1-diol n-propyl ether, tetrahydrofuran or acetone.

For the purposes of the present invention, a water-immiscible organic solvent is an organic solvent having a water solubility at atmospheric pressure of less than 10%. Possible solvents which come into consideration are, inter alia, halogenated aliphatic hydrocarbons, for example methylene chloride, chloroform and carbon tetrachloride, carboxylic esters, such as dimethyl carbonate, diethyl carbonate, propylene carbonate, ethyl formate, methyl, ethyl or isopropyl acetate, and ethers such as methyltert-butyl ether. Preferred water-immiscible organic solvents are the following compounds selected from the group consisting of dimethyl carbonate, propylene carbonate, ethyl formate, ethyl acetate, isopropyl acetate and methyltert-butyl ether.

The inventive process is preferably the production of dry powders of oxygenated carotenoids, selected from the group consisting of astaxanthin, canthaxanthin, lutein, zeaxanthin, citranaxanthin and β-apo-8'-carotenic acid ethyl ester.

Particularly preferably, in the inventive process, a) astaxanthin and/or canthaxanthin is dissolved in a water-miscible organic solvent or a mixture of water and a water-miscible organic solvent at temperatures above 30° C., b) the resultant solution is mixed with an aqueous molecular dispersion or colloidal dispersion of a partially hydrolyzed soybean protein having a degree of hydrolysis of from 6 to 9% and c) the dispersion formed is converted into a dry powder.

Very particularly preferably, this is a process for producing astaxanthin-containing dry powders.

The abovementioned dry powders are advantageously produced in such a manner that at least one of the oxygenated carotenoids is dissolved in a water-miscible organic solvent at temperatures above 30° C., preferably from 50° C. to 240° C., in particular from 100° C. to 200° C., particularly preferably from 140° C. to 180° C., if appropriate under pressure.

Since the action of high temperatures can, in some circumstances, decrease the desired high content of all-trans isomer, the carotenoid(s) is(are) dispersed as rapidly as possible, for example in a matter of seconds, for example in from 0.1 to 10 seconds, particularly preferably in less than 1 second. For rapid production of the molecular dispersion, the use of elevated pressure can be advantageous, for example in the range from 20 bar to 80 bar, preferably from 30 to 60 bar.

The resultant molecular dispersion is then admixed directly with the uncooled or cooled aqueous molecular dispersion or colloidal dispersion of the protecting colloid in such a manner that a mixture temperature of from about 35° C. to 80° C. is set.

The solvent component is transferred to the aqueous phase in the course of this and the hydrophobic phase of the carotenoid(s) is formed as nanodisperse phase.

With respect to a more detailed description of the process and apparatus regarding the abovementioned dispersion, reference is made at this point to EP B-0 065 193.

The conversion to a dry powder can be performed here inter alia by spray-drying, spray-cooling, freeze-drying or drying in a fluidized bed, in the presence or absence of a coating material. Suitable coating materials are, for example, corn starch, silicic acid, or tricalcium phosphate.

To increase the mechanical stability of the end product, it can be expedient in some cases to add to the colloid a plasticizer, such as sugars or sugar alcohols, for example sucrose, glucose, glucose syrup, dextrin, lactose, invert sugar, sorbitol, mannitol or glycerol.

To increase the stability of the active compound to oxidative degradation, it is advantageous to add stabilizers such as α-tocopherol, butylated hydroxytoluene, butylated hydroxyanisole, ascorbic acid or ethoxyquin. They can be added either to the aqueous phase or to the solvent phase, but preferably they are dissolved together with the active compound in the solvent phase.

In some circumstances it can be advantageous to dissolve, additionally in the solvent phase, a physiologically permitted oil, for example sesame oil, corn oil, cottonseed oil, soybean oil or peanut oil, and esters of medium-chain plant fatty acids, in a concentration of from 0 to 500% by weight, preferably from to 300% by weight, particularly preferably from 20 to 100% by weight, based on the xanthophyll(s), which oil is then precipitated out extremely finely divided together with the active compounds and said additives on mixing with the aqueous phase.

The ratio of protecting colloid and plasticizer to oxygenated carotenoid is generally selected so as to give an end product which comprises from 0.1 to 30% by weight, preferably from 1 to 25% by weight, particularly preferably from 5 to 20% by weight, of carotenoid, from 10 to 70% by weight of a protecting colloid, from 10 to 70% by weight of a plasticizer, with all percentages based on the dry matter of the powder, and possibly small amounts of a stabilizer.

The invention also relates to dry powders of oxygenated carotenoids obtainable by one of the processes specified at the outset.

Preferably these are dry powders comprising oxygenated carotenoids selected from the group consisting of astaxanthin, canthaxanthin, lutein, zeaxanthin, citranaxanthin and β-apo-8'-carotenic acid ethyl ester, particularly preferably canthaxanthin and astaxanthin, very particularly preferably astaxanthin.

The active compound content in the inventive dry powders is in the range from 0.1 to 30% by weight, preferably from 1 to 25% by weight, particularly preferably from 5 to 20%, by weight, very particularly preferably in the range from 8 to 15% by weight.

The inventive dry powders are distinguished, inter alia, by the fact that they can be redispersed without problem in aqueous systems to achieve a uniform fine distribution of the active compound in the particle size range less than 1 μm.

Furthermore, it has been found that colloidally stable and non-crosslinking nanoparticulate active compound dispersions of oxygenated carotenoids are obtained whose viscosity behavior approximately corresponds to that of a Newtonian liquid. Liquids of this type are distinguished by the fact that their resistance to flow defined by Newton's equation $\tau = h \cdot D$ at a given temperature is a physical constant ($\tau$=shear stress, D=shear gradient, h=dynamic viscosity). The graphical plot of the flow behavior of a Newtonian liquid gives approximately a straight line at a given temperature. In particular, the viscosity of the active compound dispersion changes by less than ±50% at 40° C. and at 60° C. in the shear range from $10^{-2}$ sec$^{-1}$ and $10^{-2}$ sec$^{-1}$ The advantages of this approximately Newtonian viscosity behavior are, inter alia, that the active compound dispersions, in particular after concentration, may be pumped more readily than is the case with intrinsically viscous dispersions. In addition, during spray-drying, the approximately Newtonian active compound dispersions have the advantage that the parameters of the spray head can be optimized more readily and that these dispersions behave less critically in the spray head.

Compared with partially hydrolyzed soybean proteins of low degrees of hydrolysis <5%, by means of the inventively used soybean proteins, xanthophyll-containing dry powders having improved color intensity and improved cold water redispersibility may be produced.

Partial hydrolyzed soybean proteins having a degree of hydrolysis greater than 5% surprisingly show a better compatibility with the water-miscible solvents mentioned at the outset. As a result, more concentrated modes of operation and thus a more economical process for producing the inventive dry powders are possible.

In addition it was found that using the inventive process the agglomeration of xanthophylls to form H aggregates is avoided.

The aggregation of carotenoids is a phenomenon which is already known in the literature and is described in numerous publications [P. Song, T. A. Moore, Photochemistry and Photobiology, 19, 435–441 (1974); A. V. Ruban, P. Horton, A. J. Young, J. Photochem. Photobiol. B: Biol., 21, 229–234 (1993); V. R. Salares, N. M. Young, P. R. Carey, H. J. Bernstein, Journal of Raman Spectroscopy, 6(6), 282–288 (1977)].

Carotenoid aggregates can be produced, for example, by mixing a solution of a carotenoid in a water-miscible organic solvent, for example isopropanol, ethanol, acetone or tetrahydrofuran, with water.

Thus, as described in the abovementioned literature, on selecting the correct mass ratios of water and organic solvent, either H or J aggregates can be produced.

H aggregates are card-stack aggregates of the polyene chains which may be characterized in the UV/Vis spectrum by the appearance of a new band in the region from 320 to 400 nm which is shifted hypsochromically compared with the absorption of the forms which occur as monomers. J aggregates, in contrast, either represent a linear head-tail aggregation of the polyenes or they are in the form of herringbone aggregates. Both arrangements produce a bathochromic shift of the UV absorption of the polyenes.

Trout feeding tests have found that H aggregates of xanthophylls, in particular the H aggregates of astaxanthin have a poorer bioavailability than the corresponding J aggregates, which is a further advantage of the dry powders produced by the inventive process.

The abovementioned dry powders are suitable in particular as additive to foods and feeds and as additive to pharmaceutical preparations. Typical fields of use for the carotenoid-containing dry powders in the animal feed sector are, for example, fish pigmentation in aquaculture and pigmentation of egg yolks and broiler skin in poultry husbandry.

In the examples below, the procedure of the inventive process is described in more detail.

EXAMPLE 1
Production of a Soybean Protein Hydrolysate by Enzymatic Degradation 600 ml of water and 40 g of soybean protein isolate (protein content 85% by weight) were charged into a 2 l glass beaker and heated to 60° C. with stirring. The pH was then adjusted to 9.0 with 1 M sodium hydroxide solution, 0.5 g of bromelain was added and the mixture was further stirred for 45 minutes at 60° C. The pH was then again adjusted to 9.0 with 1 M sodium hydroxide solution. On the basis of the sodium hydroxide solution consumption, the DH was calculated as 7%. The enzyme was then inactivated by heating the solution to 100° C. for 2 minutes.

EXAMPLE 2
Astaxanthin Dry Powder 48 g of crystalline astaxanthin and 20 g of α-tocopherol were suspended in 350 g of an azeotropic isopropanol/water mixture at room temperature in a heatable receiver at a temperature of 30° C. The active compound suspension was then heated to 100° C. and, at a flow rate of 2.1 kg/h, was continuously mixed with further isopropanol/water azeotrope at a temperature of 226° C. and a flow rate of 2.6 kg/h, with astaxanthin dissolving at a mixture temperature of 172° C. which was established at a pressure of 60 bar This active compound solution was then immediately thereafter mixed with an aqueous phase consisting of a solution of 72 g of partially hydrolyzed soybean protein having a degree of hydrolysis of 7%, 200 g of glucose syrup in 6000 g of distilled water, in which the pH had been adjusted to pH 9.5 with 1 M NaOH, at a flow rate of 35.8 kg/h.

The active compound particles formed during mixing had in the isopropanol a particle size of 174 nm water mixture, at an E1/1 value of 119.

The active compound suspension was then concentrated on a thin-film evaporator to a concentration of approximately 3.4% active compound content and spray-dried. The dry powder had an astaxanthin content of 12.3% by weight. The dry powder redispersed in water had a particle size of 200 nm and an E1/1 value of 101.

EXAMPLE 3
Astaxanthin Dry Powder 48 g of crystalline astaxanthin, 1.6 g of ascorbyl palmitate and 20 g of α-tocopherol were first suspended in 350 g of an azeotropic isopropanol/water mixture at room temperature. This active compound suspension was then heated to 88° C. and continuously mixed at a flow rate of 2.1 kg/h with further hot isopropanol/water azeotrope at a flow rate of 2.7 kg/h, astaxanthin dissolving at a mixture temperature of 165° C. which was established at a pressure of 60 bar. The active compound solution was then mixed with an aqueous phase at a flow rate of 60 kg/h consisting of a solution of 103 g of partially hydrolyzed soybean protein prepared according to example 1 and 163 g of glucose in 10800 g of distilled water, in which the pH had been adjusted to 9.5 with 1 M NaOH.

The active compound particles formed during mixing had a particle size of 153 nm in the isopropanol/water mixture, at an E1/1 value of 124. This active compound dispersion was then concentrated on a thin-film evaporator to a concentration of approximately 3.6% active compound content and spray-dried. The dry powder has an astaxanthin content of 13.0% by weight. The dry powder redispersed in water had a mean particle size of 400 nm and had an E1/1 value of 106.

EXAMPLE 4
Canthaxanthin Dry Powder 48 g of crystalline canthaxanthin, 4 g of ascorbyl palmitate and 16 g of α-tocopherol were first suspended in 350 g of an azeotropic isopropanol/water mixture at room temperature. This active compound suspension was then heated to 88° C. and, at a flow rate of 2.9 kg/h, was continuously mixed with further hot isopropanol/water azeotrope at a flow rate of 4.8 kg/h, canthaxanthin dissolving at a mixture temperature of 175° C. which was established at a pressure of 60 bar. This active compound solution was then mixed with an aqueous phase at a flow rate of 52 kg/h, consisting of a solution of 120 g of partially hydrolyzed soybean protein having a degree of hydrolysis of 7% and 197 g of glucose in 7400 g of distilled water in which the pH had been adjusted to pH 9.5 with 1 M NaOH.

The active compound particles formed during mixing had a particle size of 139 nm in the isopropanol/water mixture, at an E1/1 value of 134. This active compound dispersion was then concentrated on a thin-film evaporator of a concentration of approximately 3.3% active compound content and spray-dried. The dry powder had a canthaxanthin content of 12.5% by weight. The dry powder redispersed in water had a mean particle size of 224 nm and had an E1/1 value of 125.

EXAMPLE 5
Citranaxanthin Dry Powder 100 g of crystalline citranaxanthin, 59 g of partially hydrolyzed soybean protein having a degree of hydrolysis of 7% and 50 g of sodium ascorbate were suspended in 280 g of deionized water at room temperature. The active compound suspension was then dispersed together with approximately 400 g of zirconium oxide ceramic grinding beads of diameter 1 mm in a 1000 ml glass flask on a high-performance dispersion machine (Red-Devil®, Erichsen, Germany). After a grinding time of 1 hour, the ground suspension was added under nitrogen to an aqueous solution of 130 g of a partially hydrolyzed soybean protein having a degree of hydrolysis of 7%, 200 g of sucrose, in the presence of 1 g of ascorbyl palmitate and 1.5 g of α-tocopherol. After homogenizating the mixture, the suspension was then dried by spray-cooling. A citranaxanthin dry powder was obtained having an active compound content of 13% by weight.

We claim:

1. A process for preparing dry powders of one or more oxygenated carotenoids by
   a) suspending one or more oxygenated carotenoids in an aqueous molecular dispersion or colloidal dispersion of a protecting colloid and
   b) converting the suspension formed into a dry powder by removing water and any solvents additionally used and drying, in the presence or absence of a coating material, which comprises using as protecting colloid in process step a) at least one partially hydrolyzed soybean protein having a degree of hydrolysis greater than 5%.

2. A process as claimed in claim 1, wherein the suspension produced in process step a) is ground before conversion to a dry powder.

3. A process as claimed in claim 1, wherein the production of the suspension in stage a) comprises the following steps:

a$_1$) dissolving one or more oxygenated carotenoids in a water-miscible organic solvent or in a mixture of water and a water-miscible organic solvent or a$_2$) dissolving one or more oxygenated carotenoids in a water-immiscible organic solvent and a$_3$) mixing the solution obtained after a$_1$) or a$_2$) with an aqueous molecular dispersion or colloidal dispersion of a partially hydrolyzed soybean protein having a degree of hydrolysis greater than 5%, the hydrophobic phase of the carotenoid being produced as nanodisperse phase.

4. The process as claimed claim 1, wherein the protecting colloid is at least one partially hydrolyzed soybean protein having a degree of hydrolysis of from 6 to 12%.

5. A process as claimed in one of claims 1, wherein the oxygenated carotenoids are compounds selected from the group consisting of astaxanthin, canthaxanthin, lutein, zeaxanthin, citranaxanthin and β-apo-8'-carotinic acid ethyl ester.

6. A process as claimed in claim 5 wherein a) astaxanthin and/or canthaxanthin is dissolved in a water-miscible organic solvent or a mixture of water and a water-miscible organic solvent at temperatures above 30° C., b) the resultant solution is mixed with an aqueous molecular dispersion or colloidal dispersion of a partially hydrolyzed soybean protein having a degree of hydrolysis of from 6 to 9% and c) the suspension formed is converted into a dry powder.

7. A process as claimed in claim 6, wherein the carotenoid is astaxanthin.

8. A dry powder of oxygenated carotenoids obtained by a process defined according to one of claim 1.

9. A dry powder as claimed in claim 8 comprising oxygenated carotenoids selected from the group consisting of astaxanthin, canthaxanthin, lutein, zeaxanthin, citranaxanthin, and β-apo-8'-carotinic acid ethyl ester.

10. A dry powder as claimed in one of claim 8, having a carotenoid content of from 0.1 to 30% by weight.

11. A dry powder as claimed in one of claim 8, comprising from 5 to 20% by weight of astaxanthin.

12. A dry powder as claimed in one of claim 8, comprising from 5 to 20% by weight of canthaxanthin.

13. Additive to food, pharmaceuticals and/or animal feed comprising the dry powder claimed in claim 8.

* * * * *